(12) United States Patent
Leyser

(10) Patent No.: US 12,084,710 B2
(45) Date of Patent: Sep. 10, 2024

(54) DIAGNOSTIC KIT FOR VISCOELASTIC ANALYSIS AND USES AND METHODS THEREOF

(71) Applicant: enicor GmbH, Munich (DE)

(72) Inventor: Harald Leyser, Steinefrenz (DE)

(73) Assignee: enicor GmbH, Munich (DE)

( * ) Notice: Subject to any disclaimer, the term of this patent is extended or adjusted under 35 U.S.C. 154(b) by 829 days.

(21) Appl. No.: 17/161,221

(22) Filed: Jan. 28, 2021

(65) Prior Publication Data

US 2021/0147901 A1   May 20, 2021

Related U.S. Application Data

(63) Continuation of application No. 15/740,460, filed as application No. PCT/EP2015/001333 on Jul. 1, 2015, now Pat. No. 10,934,574.

(51) Int. Cl.

| | |
|---|---|
| *C12Q 1/56* | (2006.01) |
| *B01L 3/02* | (2006.01) |
| *G01N 33/49* | (2006.01) |
| *G01N 33/86* | (2006.01) |

(52) U.S. Cl.
CPC ............. *C12Q 1/56* (2013.01); *B01L 3/0275* (2013.01); *G01N 33/4905* (2013.01); *G01N 33/86* (2013.01)

(58) Field of Classification Search
None
See application file for complete search history.

(56) References Cited

U.S. PATENT DOCUMENTS

| | | |
|---|---|---|
| 5,777,215 A | 7/1998 | Calatzis et al. |
| 5,844,686 A | 12/1998 | Treptow et al. |
| 6,343,717 B1 | 2/2002 | Zhang et al. |
| 6,416,716 B1 | 7/2002 | Shukla et al. |
| 6,537,819 B2 | 3/2003 | Cohen et al. |
| 2002/0081747 A1 | 6/2002 | Jacobs et al. |
| 2003/0039589 A1 | 2/2003 | Smith |
| 2003/0153084 A1 | 8/2003 | Zheng et al. |
| 2004/0071604 A1 | 4/2004 | Kolde et al. |
| 2006/0275176 A1 | 12/2006 | Horn et al. |
| 2010/0081209 A1 | 4/2010 | Brewer |
| 2010/0190193 A1 | 7/2010 | Calatzis et al. |
| 2012/0009095 A1 | 1/2012 | Burke et al. |
| 2013/0102015 A1 | 4/2013 | Schubert |
| 2016/0320415 A1 | 11/2016 | Manneh |

FOREIGN PATENT DOCUMENTS

| | | |
|---|---|---|
| FR | 2498331 | 7/1982 |
| WO | WO 2002090995 | 11/2002 |

*Primary Examiner* — Matthew D Krcha
*Assistant Examiner* — Brittany I Fisher
(74) *Attorney, Agent, or Firm* — Nutter McClennen & Fish LLP

(57) ABSTRACT

A diagnostic kit for viscoelastic analysis of a sample includes a pipette tip containing constituent (A) and a measurement cup containing constituent (B), wherein the constituents (A) and (B) are adapted to form a diagnostic composition upon combination, wherein the diagnostic composition includes an activator of coagulation and a calcium salt. A method of performing a viscoelastic analysis on a sample using such a diagnostic kit is also disclosed.

25 Claims, 4 Drawing Sheets

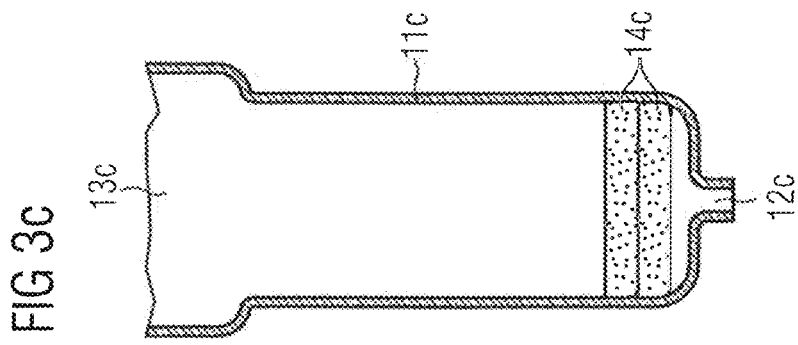
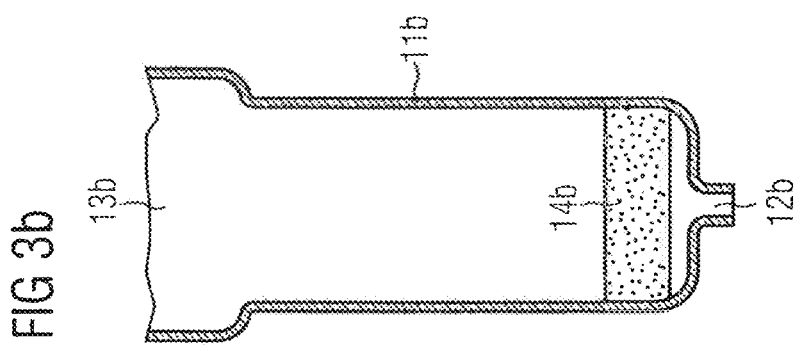
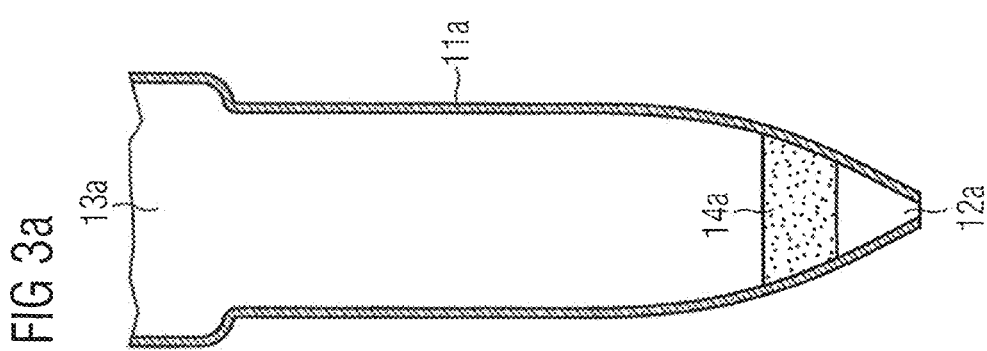

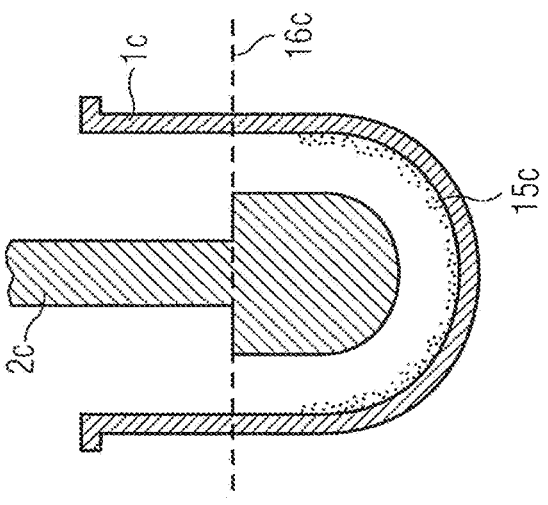
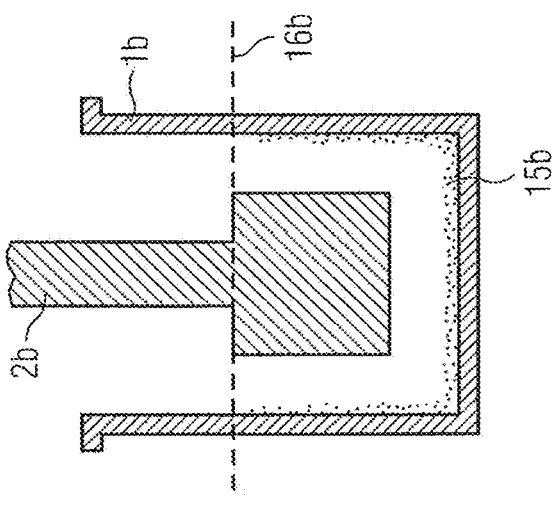
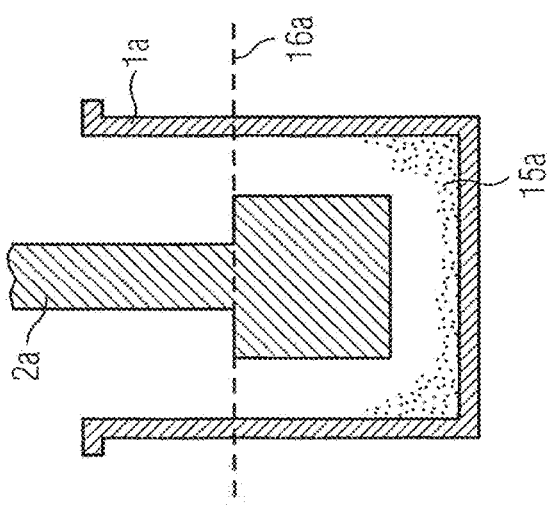

DIAGNOSTIC KIT FOR VISCOELASTIC ANALYSIS AND USES AND METHODS THEREOF

CROSS-REFERENCE TO RELATED APPLICATIONS

This application a continuation of U.S. application Ser. No. 15/740,460 filed Dec. 28, 2017, which is the U.S. national stage entry of PCT/EP2015/001333 filed Jul. 1, 2015, each of which is hereby incorporated by reference in its entirety.

The present invention relates to the field of viscoelastic analysis, in particular to hemorheology, for example to the viscoelastic analysis of blood and/or its elements, e.g. plasma and cells. The present invention is directed to a kit of special reagent containers and their content for use in viscoelastic analysis, for example in coagulation testing of sample liquids. The present invention is further directed to a method of performing such viscoelastic analysis, e.g. coagulation analysis, on a test liquid, and to the use of the kit of reagent containers in such a method.

The coagulation of blood is a highly complex process, starting with liquid blood and ending with the formation of a solid clot. It is an important part of hemostasis, i.e. the cessation of blood loss from a damaged vessel, wherein a damaged blood vessel wall is covered by a blood clot to stop hemorrhage and aid repair of the damaged vessel. Disorders in the coagulation balance can lead to increased hemorrhage and/or thrombosis and embolism.

In a normal individual, coagulation is initiated within about 20 seconds after an injury occurs to the blood vessel damaging the endothelial cells. Platelets immediately form a hemostatic plug at the site of injury. This process is called primary hemostasis. Secondary hemostasis follows if plasma components called coagulation factors respond in a complex cascade to finally form fibrin strands to strengthen the platelet plug.

The coagulation cascade of secondary hemostasis has two pathways, the Contact Activation pathway (formerly known as the Intrinsic Pathway) and the Tissue Factor pathway (formerly known as the Extrinsic pathway) that lead to fibrin formation. It was previously thought that the coagulation cascade consisted of two pathways of equal importance joined to a common pathway. It is now known that the primary pathway for the initiation of blood coagulation is the Tissue Factor pathway. The pathways are a series of reactions, in which a zymogen of a serine protease and its glycoprotein co-factor are activated to become active components, which are then able to catalyze the next reaction in the cascade. Coagulation factors are generally indicated by Roman numerals from I-XIII, with a lowercase 'a' appended to indicate the activated form. Thereby, a fibrin clot is formed, which strengthens the platelet plug.

However, to avoid thrombosis and embolism, the formation of fibrin clots is tightly controlled. The fibrin clot, i.e. the product of coagulation, is broken down in a process called fibrinolysis. Accordingly, fibrinolysis prevents blood clots from growing and becoming problematic. In fibrinolysis, the enzyme plasmin plays a major role, since plasmin cuts the fibrin mesh at various places, leading to the production of circulating fragments that are cleared by other proteases and/or by the kidney and/or liver. Plasminogen is converted to active plasmin by tissue plasminogen activator (tPA) and urokinase, thereby allowing fibrinolysis to occur.

The detection of normal or decreased functionality of these coagulation and/or fibrinolysis components is important in order to assess patients' hemostasis disorders. If a hemostasis disorder is identified, a selected therapy can be applied for example to stop a bleeding.

Several methods of measuring the coagulation characteristics of blood are known. Some such devices attempt to simulate the natural flow of blood in the veins and arteries of a living subject, while other measurement techniques are performed in static blood volumes.

An accurate measurement of the ability of a patient's blood to coagulate in a timely and effective fashion is crucial to certain surgical and medical procedures. Rapid and accurate detection of abnormal coagulations is also of particular importance with respect to appropriate treatment to be given to patients suffering from clotting disorders. Often the condition of such patients makes it necessary to administer blood components, anti-coagulants, certain fibrinolytic agents, anti-platelet agents, or compounds inducing the reverse effects of said agents. In these cases, the treatment dose can be adapted to the extent of a clotting disorder previously determined.

Measurements of blood clotting are provided by various devices, for example as disclosed in U.S. Pat. Nos. 5,777, 215 A and in 6,537,819 B2. These devices measure the mechanical properties of the clot throughout its structural development. These systems are summarized under the term "viscoelastic methods", as they continuously detect viscoelastic properties of the blood clot while its formation and lysis. Viscoelastic measurements of clotting blood are commonly also referred to as thromboelastography (TEG) measurements.

A number of references describe instruments for measuring blood clotting characteristics based upon mechanical movements. These instruments monitor the elastic properties of blood as it is induced to clot under a low shear environment, i.e. in static blood volumes. The patterns of change in shear elasticity enable the determination of the kinetics of clot formation, as well as the strength and stability of the formed clot. The strength and stability of the clot provide information about the ability of the clot to perform the "work of hemostasis" (i.e., stop or prevent abnormal bleeding) and about the adequacy of blood platelet-fibrin interaction. The kinetics of clot formation mainly provides information about the functionality of coagulation factors. Analysis of all of this information provides results which are useful to predict bleeding, to monitor and manage thrombosis, or to monitor fibrinolysis.

Moreover, as the clotting process consists of various interlinked components, specific activators and inhibitors of the clotting process may be applied in order to detect hemostasis disorders more specifically. Such reagents useful in viscoelastic analysis may comprise an initial activator (e.g., an activator of either the intrinsic or the extrinsic pathway), one or more inhibitors (e.g., fibrinolysis inhibitors, heparin inhibitors, platelet inhibitors), one or more further specific factor(s) of the coagulation cascade, calcium ($CaCl_2$), phospholipids, and/or stabilizers.

Different reagent concepts for modified viscoelastic measurements are described in the literature, including (i) Reo-Pro-modified TEG as described in Wenker et al.: Thromboelastography, The Internet journal of Anesthesiology, 2000, Volume 1 Number 3, http://www.ispub.com/ostia/index.php?xmlFilePath=journals/ija/vol1n3/teg.xml and Ruttmann et al.: Hemodilution Enhanced Coagulation Is Not Due to Platelet Clumping, Anesthesiology 2004; 101: A150; (ii) Recombiplastin- and ReoPro-modified TEG as described in http://www.transfusionguidelines.org.uk/docs/pdfs/bbt_app-use_teg-sop-example.pdf; and (iii) TF- and Trasylol-modified TEG as described in Tanaka et al.: Evaluation of a novel kallikrein inhibitor on hemostatic activation in vitro, Thrombosis Research, Volume 113, Issue 5, 2004, Pages 333-339, whereby TF- and Trasylol-modified TEG is based on the combination of commercially available activator reagents intended for other tests, such as the prothrombin time activator Innovin or Recombiplastin®, combined with customer-made $CaCl_2$ solution and drugs, such as ReoPro® (abciximab) and Trasylol® (aprotinin).

However, in those described concepts standardization is low and many complicated pipetting steps are included, resulting in many sources of user error.

There are other reagent systems on the market, which are based on a variety of reagents. For example, ROTEM® analysis (Manufacturer: Tem Innovations GmbH, Munich, Germany) provides a reagent system for viscoelastic measurements, which is based on standardized reagents, most of which are provided to the customer in a liquid form, which are pipetted by the user into the test cup using standardized operating procedures. This standardizes the application, however, it still requires several pipetting steps for the analysis. For example, to perform a platelet inhibited test together with an extrinsically activated test, the pipetting of blood, $CaCl_2$ solution, extrinsic activator and a platelet inhibitor may result in the performance of a total of eight pipetting steps (including three times changing of the tip during one test procedure) and the need for three different reagents that have to be handled by the user. This provides a requirement for training, consumes time, and is a potential source of error.

Some of the further reagent systems on the market are liquid, and have to be pipetted into a cup (e.g. $CaCl_2$ solution), some are provided in dried form in the measurement cup (such as heparinase) and some are provided in small vials, in a quantity intended for one test. A characteristic of these reagents is that still each reagent is typically provided singly, and therefore several steps are required at least for tests requiring more than one active reagent.

To provide a simpler reagent system for viscoelastic measurements of blood or blood components, the provision of stable liquid combinations of the reagents in the working concentration was investigated. However, no such stable liquid combination could be achieved due to the mutual interactions of the different substances while being mixed together for a longer period. Some components negatively affect the stability of each other when kept mixed together in the liquid phase at higher concentrations; for example, $CaCl_2$ disturbs the stability of Tissue Factor reagent in liquid phase over the time. Moreover, if these combined reagents are provided in an amount sufficient for exactly one test, another problem arises: the very small portion of a liquid reagent might stick to parts of the reagent container or the cap and might thus not mix sufficiently with the sample, i.e. the test liquid, when the analysis is performed.

To avoid these problems, Kolde et al, disclosed in US 2004/0071604 A1 a system providing freeze-dried reagents separately in their working concentrations for one test in a measurement cup (which receives the volume of the sample during measurement). In particular, Kolde et al. disclose a cup system for viscoelastic analyses, in which the lower end of the cup is divided in several sections or 'reagent chambers'. This allows to place the reagents independently into the different chambers, without mixing them and then to freeze-dry the reagents.

However, disadvantages of this solution include the need for a very precise pipetting process, as the separate reagent chambers are very small (<5 mm diameter). Another problem is that the reagent drops might 'jump' out of their section as induced by vibrations in the reagent filling line and mix with each other. A further problem is possible air-drying of the small reagent drops during the processing under room conditions before the lyophilization process begins.

Calatzis et al. disclosed in US 2010/190193 A1 another option by providing freeze-dried reagents all mixed together in their working concentrations for one test in a measurement cup or in a standard reagent container. Thereby, it is suggested that all reagents are co-lyophilized in one reagent container or directly in the measurement cup.

This approach, however, can induce instabilities and variances in the production process due to mixing of all reagents and resulting mutual interaction during the freezing process. Instabilities can also be induced during the freezing process due to corresponding well-known changes in the pH conditions of the reagent mix. Accordingly, Calatzis et al. suggested to stabilize the production process by diluting the reagent mix well below the concentration that is required in viscoelastic testing and compensate for the lower reagent content by proportionally increasing the lyophilized volume. But since the costly freeze-drying process is disproportionally prolonged by such volume increases, this approach reduces the production efficiency considerably. Moreover, co-lyophilized formulations can be substantially less stable than the separated components depending on the residual moisture in the lyophilized reagent compound, which requires even longer processing time during production.

One further shortcoming of the systems disclosed in US 2004/0071604 A1 and in US 2010/190193 A1 is that protein stabilizers are required that can later interfere with the adhesion strength of the blood clot on the cup surface during the viscoelastic measurement.

To overcome the above-mentioned problems, Schubert et al. disclosed a further option in US 2013/102015 A1, where each reagent is diluted separately in an excipient solution and lyophilized in the form of small pellets made of the excipient framework. This approach keeps the reagents apart during the whole production process as well as during storage and minimizes in this way all mutual interactions. On the other hand, an additional component—the excipient—has to be added and must be extensively verified for eventual interference with the coagulation characteristics. Besides this, the process of pellet production becomes considerably more costly than liquid dispensing. It requires highly individual equipment for both, pellet production and later pellet distribution into reagent containers or measurement cups.

In view of the above, it is the object of the present invention to overcome the drawbacks of current reagent systems for viscoelastic analysis outlined above and to provide a diagnostic kit for viscoelastic analysis, and methods and uses thereof, which are simplifying viscoelastic analysis, for example by minimizing the number of pipetting steps. Moreover, it is an object of the present invention to provide a diagnostic kit for viscoelastic analysis, wherein the required reagent composition has an improved long-term stability but does not require costly manufacturing equipment or additional (excipient) materials in the reagent composition. It is also an object of the present invention to provide a diagnostic kit for viscoelastic analysis, and methods and uses thereof which allow for a safe, reproducible and easy to use procedure for different tests. It is also an object of the present invention to provide a diagnostic kit for viscoelastic analysis, and methods and uses thereof which require only standard filling and drying procedures during production without individually specialized and costly automation equipment and allows cost-saving production. It is a further object of the present invention to provide a diagnostic method, which provides reliable and reproducible results, is easy to handle and which provides a standardized system for the determination of the coagulation characteristics of a blood sample.

This is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Diagnostic Kit for Viscoelastic Analysis

In a first aspect the present invention provides a diagnostic kit for viscoelastic analysis of a sample comprising:
a) a pipette tip containing constituent (A); and
b) a measurement cup containing constituent (B),
wherein the constituents (A) and (B) are adapted to form a diagnostic composition upon combination, wherein the diagnostic composition comprises at least the following components (i) and (ii):
  i) an activator of coagulation; and
  ii) a calcium salt.

In other words, the constituents (A) and (B) are adapted to form a diagnostic composition upon combination of the constituents (A) and (B), i.e. the diagnostic composition corresponds in particular to a combination of the constituents (A) and (B). Thus, the components comprised by the diagnostic composition are comprised by one or both of the constituents (A) and (B).

Preferably, the diagnostic kit for viscoelastic analysis of a sample according to the present invention comprises:
a) a pipette tip containing constituent (A) and not containing the constituent (B); and
b) a measurement cup containing constituent (B) and not containing the constituent (A),
wherein the constituents (A) and (B) are adapted to form a diagnostic composition upon combination, wherein the diagnostic composition (i.e. the constituents (A) and/or (B)) comprises the following components (i) and (ii):
  i) an activator of coagulation; and
  ii) a calcium salt.

Preferably, in the diagnostic kit according to the present invention as described above, the constituent (A) is different from the constituent (B). In other words, constituents (A) and (B) are preferably not the same.

Since the constituents (A) and (B) are adapted to form a diagnostic composition upon combination, wherein the diagnostic composition comprises the components (i) and (ii), as described above, each of the constituents (A) and (B) is in particular a composition of components (or reagents) by itself. In particular, constituent (A) is a composition comprising component (i) or component (ii), and, optionally, further components. Accordingly, constituent (B) is in particular a composition comprising component (i) or component (ii), and, optionally, further components. However, constituent (A) is preferably different from constituent (B) and, thus, it is preferred that:
1) component (i) is comprised by constituent (A) and component (ii) is comprised by constituent (B); or
2) component (ii) is comprised by constituent (A) and component (i) is comprised by constituent (B).

An exemplary diagram showing a typical viscoelastic analysis (also referred to as viscoelastic measurement) is shown in FIG. 1. The diagram curve represents the increasing clot firmness in the measurement cup after an initial delay time (clotting time). The curve develops until a maximum is reached that represents the maximum clot firmness of the sample.

By using the diagnostic kit according to the present invention, a viscoelastic analysis may be performed for example as follows:
1) a defined volume of a sample (e.g., whole blood, blood plasma etc.) is aspirated into a pipette tip containing constituent (A) of the diagnostic composition in dry, wet, or other formulation, thereby obtaining a mixture of constituent (A) and the sample;

2) optionally, a short time delay (e.g., 0-30 s) allows for complete dissolution of constituent (A) of the diagnostic composition within the sample liquid;
3) the mixture (or solution) of constituent (A) and the sample is added directly into a measurement cup containing a constituent (B) of the diagnostic composition in dry, wet, or other formulation, thereby obtaining a mixture of constituent (A), the sample, and constituent (B);
4) optionally, a short time delay (0-30 s) allows for mixing, preferably dissolving, of constituent (B) of the diagnostic composition within the mixture of constituent (A) and the sample;
5) optionally, to improve the mixing of all components, the resulting mixture is at least partially aspired again into a pipette tip and subsequently released again into the measurement cup (this step may be repeated one or more times); and
6) the viscoelastic measurement is started (after placing the cup in the right measurement position if this has not been done before).

Optionally, the sample may be added to a third reagent container containing a further constituent of the diagnostic composition after step 2) and aspired again after a short dissolution time (0-30 s) and before step 3).

Accordingly, the user needs only a minimum of two pipetting steps for each test to perform, while in the liquid reagent system according to the prior art up to eight steps are required. Moreover, no change of the pipette tip is necessary. Thus, the present kit—for example for the determination of coagulation characteristics of a blood sample—can be handled easier, thereby decreasing the likelihood of errors, which can be due to an imprecise line of action by a (potentially less experienced) operator. Therefrom, further advantages may arise as, for example, a higher reproducibility of the results to be achieved, and thus, a higher degree of standardization.

The sample to be tested by use of the kit according to the present invention is preferably liquid. Accordingly, it is also referred to herein to a liquid sample as sample liquid or test liquid. More preferably the sample liquid is a biofluid (also referred to as body fluid), i.e. a fluid originating from an organism, in particular a fluid originating from a human or an animal. Even more preferably the sample liquid is blood, preferably whole blood, or one or more of its elements, e.g. plasma and/or cells. Particularly preferably the sample is a human blood sample and comprises (whole) blood and/or blood plasma.

Accordingly, the present invention is directed to a diagnostic composition and reagent containers, i.e. a pipette tip and a measurement cup, for use in the viscoelastic analysis of a sample. The diagnostic composition contains at least one activator of coagulation and a calcium salt, i.e. components (i) and (ii). Optionally, the diagnostic composition may contain further components as described below, e.g. one or more other inhibitors and/or coagulation components. According to the present invention, the components of the diagnostic composition are separated into at least two reagent containers, whereby the at least two reagent containers comprise two (modified) items that are to be used anyway to perform a viscoelastic measurement: a pipette tip and the measurement cup. Thus, no additional reagent containers are necessary and a loss of diagnostic composition or one or more components thereof, which is due to pipetting from one additional reagent container into another reagent container, can be avoided. Moreover, the present invention allows to provide the required diagnostic composition with improved long-term stability and increased reconstitution time for the contained bio-molecules, but without the need for using costly manufacturing equipment or additional (excipient) materials in the reagent composition. In clinical application of the disclosed kit, the number of pipetting steps is minimized. In particular, the diagnostic kit according to the present invention is adapted to one single analysis of a blood sample and has a superior reagent stability regarding several prior art compositions. The inventive concept is based on the separation of the required substances into two different containers, i.e. into the pipetting tip, e.g. as commonly used for (liquid) pipetting, and the measurement cup, e.g. as commonly used for viscoelastic measurements.

Optionally, the diagnostic kit according to the present invention may preferably contain one or more further reagent container(s), e.g. 1, 2, 3, 4, or 5 further reagent container(s), in addition to the pipette tip containing a constituent (A) and the measurement cup containing a constituent (B). Such an additional reagent container is preferably a regular reagent vial.

Alternatively, it is preferred that the diagnostic kit according to the present invention does not contain any further reagent container in addition to the pipette tip containing a constituent (A) and the measurement cup containing a constituent (B). This means in particular that no further reagent container is required for using a diagnostic composition in the viscoelastic analysis ("using" includes herein for example: storage of the diagnostic composition or its components; preparation of the diagnostic composition or its components, including, e.g., dilution of the composition or its components, mixing of components or any pretreatment of the diagnostic composition or its components; contacting of the diagnostic composition or its components with the sample; and/or performing the measurement). The pipette tip, which contains a constituent (A), and the measurement cup, which contains a constituent (B), are in particular needed anyway to perform a viscoelastic measurement, while all other reagent containers used to perform viscoelastic testing as described in the prior art require at least one additional reagent container. In other words, it is preferred that the diagnostic kit according to the present invention comprises exactly two reagent containers, namely, the pipette tip containing a constituent (A) and the measurement cup containing a constituent (B).

Preferably, the pipette tip, which contains a constituent (A), and the measurement cup, which contains a constituent (B), and any optional additional reagent container, contain in particular a constituent of the diagnostic composition in an amount sufficient for performing one single viscoelastic analysis of a sample, in particular test liquid. In particular, the pipette tip, which contains a constituent (A), and the measurement cup, which contains a constituent (B), and any optional additional reagent container, can be filled with reagents in either liquid, dry, essentially dry or any other formulation.

The amount sufficient for performing one single viscoelastic analysis of a sample, for example a blood sample, is that amount required for each of the constituents when all constituents are in mixture (i.e. in the "diagnostic composition"), which provides the required concentration of the reagents in the final viscoelastic analysis of the sample, e.g. of a blood sample, for example in the measurement cup. Therefore, it is not necessary to further portion the diagnostic composition before or after mixing, preferably dissolving, it in a liquid.

Further, this is preferably achieved by mixing, preferably dissolving, the substances in the sample, in particular in test liquid (blood sample etc.) itself, not by mixing/dissolving the constituents in an amount of liquid diluent leading to the final working concentration.

Accordingly, the present invention (1) allows a separation of certain reagent ingredients that influence each other, which increases the reagent stability; (2) allows the formulation of ingredients in either liquid, dry, essentially or other form depending on the their stability and/or stability needs (in particular, some of the ingredients are typically used in huge excess so that partial degradation is not falsifying the test results, some ingredients are typically incredibly stable even in liquid form, and only some ingredients are typically less stable in liquid form and not used in excess and must therefore be treated more carefully); and (3) saves additional costs and material waste (i.e., reagent vials) by employing containers that are used anyway for performing the viscoelastic tests.

Accordingly, the present invention provides a unique combination of two containers, each used anyway to perform a viscoelastic measurement, namely the pipette tip, which contains a constituent (A), and the measurement cup, which contains a constituent (B). The resulting degree of freedom to formulate the at least two separated parts (i.e. the at least two separated constituents) of the diagnostic composition in either dry, essentially dry, liquid, or any other formulation comprises a complete new and highly cost-effective approach. The present inventors surprisingly arrived at the present invention based on performing a combination of analyses of the mutual ingredient interactions, performing stability studies in dependence on the formulation as dry, essentially dry or liquid, investigating stability and test performance studies to assess the possible negative impact of the employed containers on the test result in viscoelastic measurements with body liquids like blood or blood plasma (cf. Examples) and, last but not least, understanding the commercial impact on providing a reagent in either excess amount or not.

"Essentially dry" as used herein refers to a state, wherein the mixture is essentially free from any liquid or moisture, in particular being depleted of water. Water or any other liquid, however, may be present as residue in the mixture, but only to an extent, which does not negatively influence the stability of the overall composition. In particular, it has to be excluded that an interaction occurs between the different constituents, which negatively affects the stability. A remaining amount of liquid, preferably water, in the composition of up to 10% by weight may be acceptable in an essentially dry formulation.

In the diagnostic kit according to the present invention as described herein it is preferred that each of the constituents (A) and (B) is independently from each other a liquid formulation, an essentially dry formulation, or a dry formulation. More preferably either (1) constituent (A) is a liquid formulation and constituent (B) is an essentially dry formulation; or (2) constituent (A) is an essentially dry formulation and constituent (B) is a liquid formulation.

Preferably, the pipette tip is a regular pipette tip, which may be modified to incorporate a constituent (A) of a diagnostic composition. Preferably, the measurement cup is a regular measurement cup for viscoelastic testing, which may be modified to incorporate constituent (B) of a diagnostic composition.

Preferably, in the diagnostic kit according to the present invention:
1) constituent (A) comprises component (i) but not component (ii) and constituent (B) comprises component (ii) but not component (i); or
2) constituent (A) comprises component (ii) but not component (i) and constituent (B) comprises component (i) but not component (ii), Thereby, it is understood, that in situation 1), i.e. if component (i) is comprised by constituent (A) and component (ii) is comprised by constituent (B), the constituent (A) does not comprise component (ii) and the constituent (B) does not comprise component (i). Accordingly, in situation 2), i.e. if component (ii) is comprised by constituent (A) and component (i) is comprised by constituent (B), the constituent (A) does not comprise component (i) and the constituent (B) does not comprise component (ii). Thus, each of the constituents (A) and (B) preferably comprises either component (i) or component (ii).

According to the present invention component (i) of the diagnostic composition, i.e. the activator of coagulation, is preferably spatially separated from component (ii) of the diagnostic composition, i.e. the calcium salt. If these components remain spatially separated until shortly before the viscoelastic analysis starts, a superior stability of the diagnostic composition (or the respective components) can be achieved and stability related problems can be avoided. Thus, the constituent (A) of the diagnostic composition preferably comprises either component (i) or component (ii), but not both, component (i) and (ii). Accordingly, the constituent (B) of the diagnostic composition preferably comprises the component selected from component (i) and component (ii), which is not comprised by constituent (A), and also not both, component (i) and (ii).

Although certain embodiments may be preferred, as described below, in general either the activator of coagulation (component (i)) may be contained in constituent (A) in the pipette tip and the calcium salt (component (ii)) may be contained in constituent (B) in the measurement cup or vice versa.

Diagnostic Composition and Constituents and Components Thereof

In the context of the present invention, the term "diagnostic composition" refers to a reagent composition (reagent mixture) for viscoelastic analysis, in particular for viscoelastic measurement, which is ready-to-use. In other words, in addition to the diagnostic composition and the sample no further reagent is required to perform the viscoelastic analysis. Moreover, dilution or the like of the diagnostic composition is not necessary.

In the present invention, the constituents of the diagnostic composition, in particular the constituent (A) and the constituent (B), are spatially separated. As long as the constituents, in particular the constituent (A) and the constituent (B), are spatially separated, they do not yet form a diagnostic composition, however, they are able to form a diagnostic composition. The diagnostic composition is formed by bringing the constituents, e.g. constituent (A) and constituent (B), into contact with each other, preferably by mixing.

The sample may be brought into contact either (i) with the diagnostic composition, i.e. after contacting the constituents of the diagnostic composition with each other, or (ii) with a constituent, e.g. with constituent (A) or constituent (B). In case (ii) the diagnostic composition is formed after contacting the sample with one of the constituents, i.e. the sample is brought into contact with one of the constituents, e.g. with constituent (A), and the other constituent, e.g. constituent (B), is contacted thereafter with a mixture of constituent (A) and the sample, thereby forming a mixture of the diagnostic composition and the sample.

According to the present invention, the pipette tip contains constituent (A). Since the sample is typically aspirated by the pipette tip before it contacts the measurement cup, it is preferred in the present invention that the sample first contacts constituent (A), preferably in the pipette tip, and a mixture of the sample and constituent (A) then contacts constituent (B), preferably in the measurement cup. Thereby, a mixture of the diagnostic composition and the sample is formed, preferably in the measurement cup.

As described above, a diagnostic composition comprises components, which are described in more detail below. Since the constituents of the diagnostic composition are to form the diagnostic composition, the constituents, in particular constituent (A) and constituent (B), comprise the components of the diagnostic composition. Thereby, one or more components of the diagnostic composition may be comprised by constituent (A), one or more components of the diagnostic composition may be comprised by constituent (B), and one or more components of the diagnostic composition may be comprised by both, constituents (A) and (B).

Thus, it is understood, that a component "comprised by the diagnostic composition" is a component, which is comprised by one or both of the constituents, i.e. by the constituents (A) and/or (B). In other words, if the diagnostic composition comprises a certain component, this component is usually comprised by constituent (A) (and not by constituent (B)) or by constituent (B) (and not by constituent (A)) or by both, constituent (A) and (B).

The diagnostic composition for viscoelastic analysis, i.e. the constituents (A) and/or (B), comprise(s) (i) an activator of coagulation (e.g., an activator of either the intrinsic or the extrinsic pathway), (ii) a calcium salt, and (iii) optionally one or more further inhibitors, e.g. fibrinolysis inhibitors, platelet inhibitors, heparin inhibitors and/or (iv) optionally one or more further specific factor of the coagulation cascade.

Preferably, the activator of coagulation is an extrinsic activator and/or an intrinsic activator, i.e. an activator of the extrinsic pathway (the Tissue Factor pathway) or of the intrinsic pathway (the Contact Activation pathway).

Thereby, it is preferred in a diagnostic kit according to the present invention as described above that:
component (i) is an extrinsic activator of coagulation and component (ii) is a calcium salt; or
component (i) is an intrinsic activator of coagulation and component (ii) is a calcium salt.

The extrinsic activator of coagulation maybe an activator of the Extrinsic Prothrombin Activation Pathway (extrinsic pathway), in particular a Tissue factor (TF, also referred to as platelet tissue factor, factor III, thromboplastin, or CD142). Preferably, the TF is selected from lipidated TF or recombinant TF (rTF).

The intrinsic activator of coagulation maybe any activating factor of the Contact Activation pathway (intrinsic pathway), e.g., celite, ellagic acid, sulfatit, kaolin, silica, or RNA. Preferably, the intrinsic activator of coagulation is selected from celite, ellagic acid, sulfatit, kaolin, silica, or mixtures thereof.

The diagnostic kit according to the present invention as described herein may contain a calcium salt, preferably as component (ii). The calcium salt is added for re-calcification of the sample. Blood samples can be prevented from clotting by several different anticoagulatory substances like heparin, EDTA, citrate. Typically functional tests are performed with blood anticoagulated with citrate. Citrate moderately complexes calcium of the blood sample. Calcium is necessary for the coagulation process, it is involved in complex formation and is a co-factor for most of the coagulation factors (e.g., FI, FII, FV, FVII, FVIII, FIX, FX, FXI, FXIII, TF). Therefore, recalcification of the sample is necessary to ensure correct coagulation in the sample, if the sample was for example citrated during blood withdrawal (by using a blood tube containing citrate). Preferably, the calcium salt is calcium chloride and/or calcium lactate and/or calcium gluconate. More preferably, the calcium salt is $CaCl_2$.

Preferably, the calcium salt, in particular $CaCl_2$, is present in an amount of about 1-100 µmol/ml of sample (test liquid), more preferably in an amount of about 3-30 µmol/ml of sample (test liquid). As mentioned above, the amount of the calcium salt, in particular $CaCl_2$, must be sufficient to ensure recalcification of the sample, in particular of the blood sample, if the sample was decalcified before. It turned out that an amount of from 3-30 µmol/ml is particularly optimal to achieve this requirement. In order to determine the required amount of the calcium salt, in particular $CaCl_2$, to be contained in the diagnostic composition, i.e. the constituents (A) and/or (B), even more precisely, the exact volume of the sample to be collected from the patient has to be known as well as the amount of decalcifying reagent employed.

The diagnostic composition, i.e. the constituents (A) and/or (B), may optionally comprise further components. Preferably, the diagnostic composition, i.e. the constituents (A) and/or (B), further comprises one or more components selected from the group consisting of: a further activator of coagulation (i.e. an activator of coagulation as described herein, which is different from the activator of coagulation comprised as component (i); a coagulation inhibitor (i.e., a substance that stops, reduces, or at least modifies the function of a certain components of the coagulation and/or clot lysis cascade); and an active-component inhibitor (i.e., a substance the stops, reduces, or at least modifies the function of a component active in coagulation, e.g. a coagulation inhibitor). Preferably, the coagulation activating factor is selected from the group consisting of FI, FII, FV, FVII, FVIII, FIX, FX, FXI, FXIII, and TF. Preferably, the coagulation inhibitor is selected from the group consisting of tissue factor pathway inhibitor, antithrombin I-IV, or activated protein C.

Preferably, the active-component inhibitor is selected from the group consisting of one or more platelet inhibitors (i.e., substances that stop, reduce, or at least modify the function of thrombocytes), one or more fibrinolysis inhibitors (i.e., substances that stop, reduce, or at least modify the function of clot lysis), and/or one or more heparin inhibitors. Preferably, the platelet inhibitor is a cytoskeleton inhibitor, preferably Cytochalasin D, or a GPIIb/IIIa antagonist, preferably Abciximab. Preferably, the fibrinolysis inhibitor is selected from the group consisting of aprotinin, tranexamic acid, eaca, thrombin-activated fibrinolysis inhibitor, plasminogen activation inhibitor 1/2, α2-antiplasmin, and α2-macroglobulin. Preferably, the heparin inhibitor is selected from heparinase, protamine or protamine-related peptides and their derivatives, or other cationic polymers, for example hexadimethrine bromide (polybrene). The heparin inhibitor is in particular useful to detect the presence of heparin in the sample and, thus, the amount of heparin inhibitor (e.g., heparinase) is a sufficient to detect the presence of heparin in the sample.

Those inhibitors may be used and combined depending on the precise diagnostic demands, for example, the platelet inhibitor may be a cytoskeleton inhibitor or a GPIIb/IIIa antagonist. The fibrinolysis inhibitor can be selected, for example, from aprotinine, tranexamic acid, or eaca; the heparin inhibitor might be selected, for example, from heparinase, protamine or protamine-related peptides; and the coagulation factor can be selected, for example, from one or more coagulation factors or activated coagulation factors preferably FXa or FVa or activated protein C or FVIIa. However, it is noted that this is only a preferred selection and further inhibitors can be used if required.

Preferably, the diagnostic composition, i.e. the constituents (A) and/or (B), may also contain one or more stabilizers, wherein the stabilizer is preferably albumin or gelatine. Such stabilizers are typically used for the stabilization of the reagents between the time of production and the analysis. Preferably, in the kit according to the present invention, a protein stabilizer, for example albumin or gelatin, is comprised by constituent (A) but is not comprised by constituent (B); or a protein stabilizer, for example albumin or gelatin, is comprised by constituent (B) but is not comprised by constituent (A).

Alternatively, it is also preferred that the diagnostic composition, i.e. the constituents (A) and/or (B), do(es) not contain albumin, more preferably the diagnostic composition, i.e, the constituents (A) and/or (B), do(es) not contain albumin or gelatin, and even more preferably the diagnostic composition, i.e. the constituents (A) and/or (B), do(es) not contain any stabilizer.

Preferably, the diagnostic composition, i.e. the constituents (A) and/or (B), may also contain one or more phospholipids. Phospholipids may be added since several complexes in the coagulation cascade are phospholipid-dependent. Preferably, the phospholipids may be a composition of different phospholipids like for example phosphatidylserine, phosphatidylethanolamine and phosphatidylethanolcholine. Preferably, mixtures of different phospholipids as extracted from biological samples (e.g., rabbit brain) may be used.

Depending on the diagnostic aim, the above described components can be used either alone or in combination: For example, a measurement with only an intrinsic activator in the sample can be combined with a measurement with an intrinsic activator and a sufficient amount of heparin inhibitor (e.g., heparinase) in the sample to detect the presence of heparin in the test liquid; a combination of extrinsic activator and platelet inhibitor (e.g., Cytochalasin D) in the sample can be applied to determine the activity of fibrinogen without platelet contribution in the sample.

Preferably, the diagnostic composition, i.e. the constituents (A) and/or (B), comprise or consist of the following combinations of components:
extrinsic activation: Combination of extrinsic activator and $CaCl_2$ and, optionally, stabilizer(s);
intrinsic activation: Combination of intrinsic activator and $CaCl_2$ and, optionally, stabilizer(s);
extrinsic activation insensitive for heparin: Combination of extrinsic activator, heparin inhibitor, $CaCl_2$ and, optionally, stabilizer(s);
intrinsic activation insensitive for heparin: Combination of intrinsic activator, heparin inhibitor, $CaCl_2$ and, optionally, stabilizer(s);
extrinsic activation without platelet activation: Combination of extrinsic activator, platelet inhibitor and $CaCl_2$ and, optionally, stabilizer(s);
extrinsic activation without platelet activation, insensitive for heparin: Combination of extrinsic activator, platelet inhibitor, heparin inhibitor, $CaCl_2$ and, optionally, stabilizer(s);
extrinsic activation without platelet activation, insensitive for heparin: Combination of extrinsic activator, platelet inhibitor, heparin inhibitor, $CaCl_2$ and, optionally, stabilizer(s);
intrinsic activation without platelet activation: Combination of intrinsic activator, platelet inhibitor, $CaCl_2$ and, optionally, stabilizer(s);
intrinsic activation without platelet activation, insensitive for heparin: Combination of intrinsic activator, platelet inhibitor, heparin inhibitor, $CaCl_2$ and, optionally, stabilizer(s);
extrinsic activation with inhibition of fibrinolysis: Combination of extrinsic activator, fibrinolysis inhibitor and $CaCl_2$ and, optionally, stabilizer(s);
extrinsic activation with inhibition of fibrinolysis, insensitive for heparin: Combination of extrinsic activator, fibrinolysis inhibitor, heparin inhibitor, $CaCl_2$ and, optionally, stabilizer(s);
intrinsic activation with inhibition of fibrinolysis: Combination of intrinsic activator, fibrinolysis inhibitor and $CaCl_2$ and, optionally, stabilizer(s);
intrinsic activation with inhibition of fibrinolysis, insensitive for heparin: Combination of intrinsic activator, fibrinolysis inhibitor, heparin inhibitor, $CaCl_2$ and, optionally, stabilizer(s);
extrinsic activation with additional coagulation factor: Combination of extrinsic activator, one additional coagulation factor and $CaCl_2$ and, optionally, stabilizer(s);
extrinsic activation with additional coagulation factor, insensitive for heparin: Combination of extrinsic activator, one additional coagulation factor, heparin inhibitor, $CaCl_2$ and, optionally, stabilizer(s);
intrinsic activation with additional coagulation factor: Combination of intrinsic activator, one additional coagulation factor and $CaCl_2$ and, optionally, stabilizer(s);
intrinsic activation with additional coagulation factor, insensitive for heparin: Combination of intrinsic activator, one additional coagulation factor, heparin inhibitor, $CaCl_2$ and, optionally, stabilizer(s).

Pipette Tip

The diagnostic kit according to the present invention comprises a pipette tip, which contains constituent (A) and which is described in the following in more detail.

As used herein, a "pipette tip" is the tip of a pipette. A pipette is a laboratory tool commonly used to transport a measured volume of liquid. Pipettes come in several designs for various purposes with differing levels of accuracy and precision, from single piece glass pipettes to more complex adjustable or electronic pipettes. Many pipette types work by creating a partial vacuum above the liquid-holding chamber and selectively releasing this vacuum to draw up and dispense liquid. Measurement accuracy varies greatly depending on the style.

Preferably, the pipette is an air-displacement micropipette, which is a type of adjustable micropipette that measures volumes between about 0.1 μl-1000 μl (1 ml). These pipettes require disposable tips that come in contact with the fluid. The four standard sizes of micropipettes correspond to four different disposable tip colors:
(1) Pipette "P10" for pipetting a volume of 0.5-10 μl, whereby the corresponding tips are usually of white color;

(2) Pipette "P20" for pipetting a volume of 2-20 μl, whereby the corresponding tips are usually of yellow color;
(3) Pipette "P200" for pipetting a volume of 20-200 μl, whereby the corresponding tips are usually of yellow color; and
(4) Pipette "P1000" for pipetting a volume of 200-1000 μl, whereby the corresponding tips are usually of blue color.

Accordingly, the diagnostic kit according to the present invention preferably comprises a pipette tip containing a constituent (A), wherein the pipette tip is preferably a disposable pipette tip, more preferably a disposable pipette tip for an air-displacement micropipette, even more preferably a disposable pipette tip for an air-displacement micropipette for pipetting a volume of 10-300 microliter.

It is also preferred that the pipette tip is the tip of any other pipette, for example the tip of a positive displacement pipette, preferably a disposable tip of a positive displacement pipette, which is in particular a microsyringe (plastic), composed of a plunger which directly displaces the liquid; the tip of a volumetric pipette, the tip of a graduated pipette, or any other type of pipette. Thereby, it is preferred that it is a disposable pipette tip.

In general, the pipette tip in the diagnostic kit according to the present invention, which contains constituent (A) of the diagnostic composition comprises:
an open upper end fitting to the corresponding end of a pipette;
an open lower end; and
a region of the inner surface of the pipette tip containing the constituent (A) directly on said inner tip surface, and/or an insert containing the constituent (A) of the diagnostic composition and keep it for the allowed storage time of the tip, whereby the insert preferably comprises a porous structure, preferably of a natural or artificial polymer.

Preferably, the open upper end of the pipette tip and the open lower end of the pipette tip have a circular shape. It is also preferred that the open lower end of the pipette tip has a smaller diameter than the open upper end.

Preferably, in the diagnostic kit according to the present invention, the shape of the pipette tip containing the constituent (A) is adapted to receive a porous insert, whereby the porous insert preferably has a cylindrical shape. Thus, it is preferred that the shape of the tip is modified in comparison to the shape of a regular conical pipette tip in a way that the insert can be made of a cylindrical shape. In particular, it is preferred that such a preferred modified pipette tip has as a barely conical, but nearly cylindrical shape, more preferably a cylindrical shape, over at least 2 mm of its entire length. Such a modified pipette tip can receive a cylindrical insert, and a conical shape of the insert can be avoided. Cylindrical inserts are easier and cheaper to produce than conical inserts because they can be blanked directly from sheet material.

The position of the region of the inner surface of the pipette tip containing the constituent (A) and the position of the insert within the tip, respectively, are variable, but it is in particular at least in the range where the sample liquid (in an amount as required to perform the viscoelastic test) can completely wet the region or insert. Thus, the position of the region supposed to receive the constituent (A) or the insert within the tip is preferably within the lower half of the pipette tip, more preferably within the lowest third of the pipette tip, even more preferably within the lowest quarter (fourth) of the pipette tip, whereby the terms "half", "third" and "quarter (fourth)" refer to the respective volume in relation to the total volume of the pipette tip, i.e. ½ of the total volume, ⅓ of the total volume or ¼ of the total volume.

It is also preferred that the pipette tip containing the constituent (A) comprises at least one porous insert with pore sizes preferably in the range of 3 to 500 micrometers, whereby the insert preferably contains the constituent (A). In particular, the insert is preferably a porous substrate with pores of sizes >3 micrometer and <500 micrometer. Preferably such an insert, i.e. an insert having such pore sizes, is made of a plastic material that can be injection-molded, sintered, extruded or foamed with the formation of continuous porosity of above mentioned sizes. Examples of such a plastic material, which is the preferred material of the insert, include polyethylene, polypropylene polycarbonate, polyether, polyesther, and the like. It is also preferred that the insert is not made of a material containing glass or metal, e.g. sheet metal and/or aluminum foil, more preferably the insert does not contain any glass or metal, e.g. sheet metal and/or aluminum foil. It is also preferred that the pipette tip is not made of a material containing glass or metal, e.g. sheet metal and/or aluminum foil, more preferably the pipette tip does not contain any glass or metal, e.g. sheet metal and/or aluminum foil.

Preferably, those reagent components that benefit from longer reconstitution or incubation times are comprised by constituent (A) and placed in the reagent-containing tip. For example, phospholipids will benefit from longer reconstitution times (to form more stable micelles), or heparin inhibitors, e.g. hexadimethrine bromide (polybrene) and heparinase, will benefit from a longer incubation time in the sample (to fully inactivate the present heparin). Thus, if a phospholipid and/or a heparin inhibitor, preferably heparinase and/or hexadimethrine bromide (polybrene), more preferably hexadimethrine bromide (polybrene), are comprised by the diagnostic composition as described herein, it is preferred that the phospholipid and/or the heparin inhibitor, preferably heparinase and/or hexadimethrine bromide (polybrene), more preferably hexadimethrine bromide (polybrene), are comprised by constituent (A) and placed in the pipette tip.

Preferably, the pipette tip, in particular constituent (A), does not contain protein stabilizers like albumin. Such stabilizers may interfere with viscoelastic measurement.

Preferably, the pipette tip, in particular constituent (A), comprises component (i), but not component (ii). In other words, it is preferred that the pipette tip, in particular constituent (A), comprises an activator of coagulation, but not a calcium salt. More preferably, the pipette tip, in particular constituent (A), comprises at least an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid. This embodiment is referred to as 'EX-tip' in the following.

It is also preferred that the pipette tip, in particular constituent (A), contains in addition to component (i), i.e. the activator of coagulation (preferably the extrinsic activator of coagulation, more preferably TF, lipidated TF or rTF and even more preferably TF), one or more platelet inhibitors, preferably selected from GPIIb/IIIa antagonists, preferably Abciximab, and/or cytoskeleton inhibitors, preferably Cytochalasin D, in dry, essentially dry, or liquid formulation, or in any other formulation that allows for dissolution of the reagent composition within 30 s after aspiration of the sample liquid. This embodiment is referred to as 'FIB-tip' in the following.

It is also preferred that the pipette tip, in particular constituent (A), contains in addition to component (i), i.e. the activator of coagulation (preferably the extrinsic activator of coagulation, more preferably TF, lipidated TF or rTF and even more preferably TF), one or more lysis inhibitors, preferably aprotinine, tranexamic acid or eaca, in dry, essentially dry, or liquid formulation, or in any other formulation that allows for dissolution of the reagent composition within 30 s after aspiration of the sample liquid. This embodiment is referred to as 'AP-tip' in the following.

It is also preferred that the pipette tip, in particular constituent (A), in particular the constituent (A) according to the three previously described preferred embodiments, contains in addition one or more heparin inhibitors, preferably protamine or protamine derivates, whereby preferred protamine derivatives include protamine sulfate and protamine hydrochloride, or other protamine-like peptides and their derivatives, or other cationic polymers, preferably hexadimethrine bromide (polybrene), that have the potential to neutralize the anti-coagulating effect(s) of heparine or heparine-like substances in a blood sample by charge interaction. The resulting reagent composition is preferably a dry, essentially dry or a liquid formulation, or any other formulation that allows for dissolution of the reagent composition within 30 s after aspiration of the sample liquid. Corresponding tips are referred to as 'EX-tip HI', 'FIB-tip HI', and 'AP-tip HI' in the following.

It is also preferred that the pipette tip, in particular constituent (A), comprises at least an intrinsic activator of coagulation, which is preferably selected from celite, ellagic acid, sulfatit, kaolin, silica, RNA, or any mixtures thereof in dry, essentially dry, or liquid formulation, or in any other formulation that allows for dissolution of the activator within 30 s after aspiration of the sample liquid. This embodiment is referred to as 'IN-tip' in the following.

Preferably, the pipette tip, in particular constituent (A), comprises in addition to component (i), i.e. the activator of coagulation (preferably the intrinsic activator of coagulation, more preferably celite, ellagic acid, sulfatit, kaolin, silica, RNA, or any mixtures thereof), one or more heparin inhibitors, preferably heparinase, protamine, or protamine-related peptides, in dry, essentially dry or liquid formulation, or in any other formulation that allows for dissolution of the activator within 30 s after aspiration of the sample liquid. This embodiment is referred to as 'HEP-tip' in the following.

It is also preferred that the pipette tip, in particular constituent (A), comprises component (ii), but not component (I). In other words, it is preferred that the pipette tip, in particular constituent (A), comprises a calcium salt, but not an activator of coagulation. Preferably the calcium salt is selected from $CaCl_2$, Calcium-Lactate, Calcium-Gluconate, or any mixtures thereof in dry, essentially dry, or liquid formulation, or in any other formulation that allows for dissolution of the activator within 30 s after aspiration of the sample liquid. This embodiment is referred to as 'CA-tip' in the following.

If constituent (A) as described above comprises more than one component, the components may (1) either be combined, e.g. mixed, with each other and placed into the pipette tip, preferably within the same (single) porous insert, or, (2) one or more or each of the components may be placed in a separate insert within the tip. Thus, the pipette tip may contain one or more inserts, for example 1, 2, 3, 4, or 5 inserts. Preferably, the more than one components are to be combined, e.g. mixed, with each other and placed into the pipette tip, preferably within the same (single) porous insert.

It is also preferred that one or more or each of the components may be placed in a separate insert within the tip.

The first option, i.e. the combination, e.g. mixture, of all of the components constituting constituent (A) in one single insert, requires identical formulation (e.g., i.e., dry, essential dry or liquid) of all of the components constituting constituent (A). The second option, wherein one or more or each of the components is placed in a separate insert, allows the combination of (essentially) dry and liquid reagent formulations within one tip. For example, one component in a first insert is a dry or essentially dry liquid formulation, while another component in a second insert is a liquid formulation. In another example two components are mixed as liquids and one component may be dried in a separate insert.

Preferred embodiments of a pipetting tip containing constituent (A), wherein the constituent (A) is kept in a porous insert, are shown in FIG. 3. A first preferred embodiment, shown in FIG. 3a), is a pipette tip (11a) containing constituent (A), which has a regular tip shape with open lower end (12a), open upper end (13a) fitting to the pipette dimensions, and a single porous insert (14a), wherein the porous insert (14a) has a conical shape as required by the regular tip shape. Another preferred embodiment, shown in FIG. 3b), is a pipette tip (11b) containing constituent (A), which has an adapted tip shape with open lower end (12b), open upper end (13b) fitting to the pipette dimensions, and a single porous insert (14b), wherein the porous insert (14b) has a cylindrical shape as required by the adapted tip shape. Another preferred embodiment, shown in FIG. 3c), is a pipette tip (11c) containing constituent (A), which has an adapted tip shape with open lower end (12c), open upper end (13c) fitting to the pipette dimensions, and at least two porous inserts (14c), positioned adjacently to each other, wherein the porous inserts (14c) have a cylindrical shapes as required by the adapted tip shape.

Measurement Cup

The diagnostic kit according to the present invention comprises a measurement cup, which contains constituent (B) and which is described in the following in more detail.

As used herein, a "measurement cup" is a cup that receives the sample liquid to be measured in the viscoelastic test. Preferably, the measurement cup is a plastic cup, more preferably the measurement cup is a disposable plastic cup.

Preferably, the measurement cup is made of a plastic material that can be injection-molded. Preferably, the cup is made of an injection-molding compatible polymer material that allows for proper anchorage of the blood clot on its surface, preferred examples include polystyrene (PS), polymethyl methacrylate (PMMA), methyl methacrylate acrylonitrile butadiene styrene (MABS), polyimide (PA), polysulfone, polycarbonate (PC), polyethylene (PE), polypropylene (PP), or the like. It is also preferred that the measurement cup is not made of a material containing glass or metal, e.g. sheet metal and/or aluminum foil, more preferably the measurement cup does not contain any glass or metal, e.g. sheet metal and/or aluminum foil.

Preferably, the measurement cup is cylindrical. The, in particular cylindrical, measurement cup containing constituent (B) preferably comprises:
  an upper open end that allows insertion of a pin prior to a viscoelastic measurement; and
  a closed lower end designed to receive constituent (B) of the diagnostic composition.

Preferably, the upper open end of the measurement cup and the closed lower end of the measurement cup have a circular shape. It is also preferred that the upper open end of the measurement cup has a diameter from 5 to 10 mm.

Moreover, it is also preferred that the diameter of the (circular) upper open end of the measurement cup is not smaller than the diameter of the (circular) closed lower end. Preferably, the measurement cup has a cylindrical shape, whereby the diameter of the (circular) upper open end of the measurement cup and the diameter of the (circular) closed lower end of the measurement cup are about the same size.

Preferably, the closed lower end of the measurement cup has no sharp edge along the border to the (cylindrical) sidewall of the measurement cup. Preferably, the closed lower end of the measurement cup has a radius of at least 0.25 mm, more preferably of about 1 mm or more, to prevent reagent clustering due to capillary forces in the corners during drying.

The term "pin" as used herein (also referred to as "measurement pin") refers to an element for performing a viscoelastic test (cf. FIG. 2). Typically, for performing a viscoelastic test the sample to be tested, e.g. a (whole) blood sample, is provided, in particular mixed with the diagnostic composition, in the measurement cup as described herein. For the viscoelastic test, typically a pin is immerged into the cup thereby in particular contacting the sample, e.g. a (whole) blood sample, in particular mixed with the diagnostic composition; preferably the pin is immerged into the sample, e.g. a (whole) blood sample, in particular mixed with the diagnostic composition. The detection of the characteristic parameters of the sample, e.g. the blood forming a clot, is typically based on the (mechanical) coupling of cup and pin which is established by the formation of e.g. a clot.

Typically, the measurement is performed in an apparatus, wherein either the pin is moved, preferably rotated, whereas the cup is stationary at the beginning or stays stationary throughout the measurement—or the cup is moved, preferably rotated, whereas the pin is stationary at the beginning or stays stationary throughout the measurement. After the formation of for example a clot between cup (cuvette) and pin, the clot itself is stretched by the movement of the pin relative to the cup or of the cup relative to the pin.

For example, the cup may rotate and the pin is stationary at the beginning, but able to rotate as well. Upon clot formation in this case the pin may typically start to rotate, which can be measured. In a preferred example, the pin rotates and the cup stays stationary throughout the measurement, whereby upon clot formation the initial unrestricted rotation of the pin starts to encounter increasing impedance as the clot strength increases, which is typically measured, e.g. by detection by an optical system.

The pin, which in particular immerges into the cup when performing a viscoelastic test, is preferably made of plastic, more preferably it is a disposable plastic element. Preferably, this pin used to perform the viscoelastic measurement has a radius of similar size, preferably of about the same size, more preferably of the same size, along its outer edge between lower end and cylindrical sidewall as the cup has along its inner edge between lower end and cylindrical sidewall (cf. FIG. 4c).

Preferably, the measurement cup containing constituent (B) comprises a reagent layer. More preferably, constituent (B) or its components are sprayed in micro-drops onto the surface of the measurement cup. Thereby, reagent clustering along the bottom edge is prevented. This furthermore allows wetting of the sidewalls and increases the covered surface, resulting in less reagent layer thickness and corresponding faster dissolution after sample adding. More preferably, the measurement cup containing a constituent (B) comprises a reagent layer that is formed by spraying of drops into the cup, whereby each of the sprayed drops has a diameter of less than 100 micrometer.

Preferably, the measurement cup containing constituent (B) comprises a reagent layer having an even thickness on the bottom and, at least partially, a minimum height of 2 mm at the sidewall. Thereby, the layer surface is increased and the layer thickness is decreased.

In the diagnostic kit according to the present invention, it is also preferred that the kit further comprises:

c) a measurement pin, in particular to perform a viscoelastic test;

wherein the measurement pin has preferably rounded edges along the contact line between bottom and sidewall. Thereby, the shape corresponds to the shape of the cup and in this way potential measurement errors are minimized. As described above, the pin has preferably a radius of similar size, in particular of about the same size, as the cup along its edge between lower end and sidewall.

Preferably, the measurement cup, in particular constituent (B), comprises component (ii), but not component (i). In other words, it is preferred that the measurement cup, in particular constituent (B), comprises a calcium salt, but not an activator of coagulation. More preferably, the measurement cup, in particular constituent (B), comprises at least a calcium salt, preferably $CaCl_2$, Calcium-Gluconate, or Calcium-Lactate or any mixtures thereof. Thereby, preferably a molar $Ca^{2+}$-concentration in the range of 1-100 μmol/ml is provided, whereby this concentration refers to the $Ca^{2+}$-concentration after mixture with constituent (A) and the sample. The exact $Ca^{2+}$-concentration is calculated to re-calcify a blood sample that has been calcium-depleted before by a $Ca^{2+}$-ion neutralizer (e.g., sodium citrate). This embodiment is referred to as 'CA-cup' in the following, and the reagent is stored therein in dry, essentially dry, or liquid formulation that allows dissolution within less than 30 s after sample aspiration into the cup.

Preferably, the measurement cup, in particular constituent (B), comprises in addition to the calcium salt (preferably $CaCl_2$, Calcium-Gluconate, or Calcium-Lactate or any mixtures thereof, more preferably in the range of 1-100 μmol/ml) one or more platelet inhibitors, preferably selected from GPIIb/IIIa antagonists, preferably Abciximab, and/or cytoskeleton inhibitors, preferably Cytochalasin D. This embodiment is referred to as 'FIB-cup' in the following, and the reagent is stored therein in dry, essentially dry, or liquid formulation that allows dissolution within less than 30 s after sample aspiration into the cup.

It is also preferred that the measurement cup, in particular constituent (B), comprises in addition to the calcium salt (preferably $CaCl_2$, Calcium-Gluconate, or Calcium-Lactate or any mixtures thereof, more preferably in the range of 1-100 μmol/ml) one or more lysis inhibitors, preferably aprotinine, tranexamic acid, or eaca. This embodiment is referred to as 'AP-cup' in the following, and the reagent is stored therein in dry, essentially dry, or liquid formulation that allows dissolution within less than 30 s after sample aspiration into the cup.

It is also preferred that the measurement cup, in particular constituent (B), in particular the constituent (B) according to the three previously described preferred embodiments, contains in addition protamine or protamine derivatives, whereby preferred protamine derivatives include protamine sulfate and protamine hydrochloride, or protamine-like peptides, or other cationic polymers, preferably hexadimethrine bromide (polybrene), that have the potential to neutralize the anti-coagulating effect(s) of heparine or heparine-like substances in a blood sample by charge interaction. These embodiments are referred to as 'CA-cup HI', 'FIB-cup HI' and 'AP-cup HI' in the following, and the reagent is stored therein in dry, essentially dry, or liquid formulation that allows dissolution within less than 30 s after sample aspiration.

It is also preferred that the measurement cup, in particular constituent (B), comprises in addition to the calcium salt (preferably $CaCl_2$, Calcium-Gluconate, or Calcium-Lactate or any mixtures thereof, more preferably in the range of 1-100 µmol/ml) heparinase (heparin lyase) or other similar lyases that have the potential to inhibit the anti-coagulating effect(s) of heparine or heparine-like substances (e.g., low-molecular weight heparines) in a blood sample by direct chemical interaction. This embodiment is referred to as 'HEP-cup' in the following, and the reagent is stored therein in dry, essentially dry, or liquid formulation that allows dissolution within less than 30 s after sample aspiration.

It is also preferred that the measurement cup, in particular constituent (B), comprises component (i), but not component (ii). In other words, it is preferred that the measurement cup, in particular constituent (B), comprises an activator of coagulation, but not a calcium salt.

Thereby, it is preferred that the measurement cup, in particular constituent (B), comprises at least an intrinsic activator of coagulation, which is preferably selected from celite, ellagic acid, sulfatit, kaolin, silica, RNA, or any mixtures thereof in dry, essentially dry, or liquid formulation, or in any other formulation that allows for dissolution of the activator within 30 s after aspiration of the sample liquid. This embodiment is referred to as 'IN-cup' in the following, and the reagent is stored therein in dry, essentially dry, or liquid formulation that allows dissolution within less than 30 s after sample aspiration.

It is also preferred that the measurement cup, in particular constituent (B), comprises at least an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid. This embodiment is referred to as 'EX-cup' in the following, and the reagent is stored therein in dry, essentially dry, or liquid formulation that allows dissolution within less than 30 s after sample aspiration.

Preferred embodiments of a measurement cup containing constituent (B), are shown in FIG. 4. A first preferred embodiment, shown in FIG. 4a, is a measurement cup (1a) containing constituent (B) in dry form (15a), which is unevenly distributed on the bottom (thicker range along the edge due to capillary forces during the drying). The dotted line (16a) indicates the filling level of the sample. Another preferred embodiment, shown in FIG. 4b, is a measurement cup (1b) containing constituent (B) in dry form (15b), which is evenly distributed on the bottom and sidewalk of the measurement cup after being sprayed in micro-drops onto the surface. The dotted line (16b) indicates the filling level of the sample. Another preferred embodiment, shown in FIG. 4c, is a measurement cup (1c) containing constituent (B), which has an adapted shape with dry constituent (B) (15c) evenly distributed on the bottom because rounded edges reduce capillary forces during drying. The dotted line (16c) indicates the filling level of the sample.

Kit Comprising the Pipette Tip and

Different preferred diagnostic kits according to the present invention as described above can be created by combining different preferred embodiments of the pipette tip containing constituent (A) as described above and different preferred embodiments of the measurement cup containing constituent (B) as described above.

Preferably, in a kit according to the present invention, the kit comprises:
  a) a pipette tip containing constituent (A) comprising an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid; but not comprising a calcium salt; and
  b) a measurement cup containing constituent (B) comprising a calcium salt, preferably $CaCl_2$, Calcium-Gluconate, or Calcium-Lactate or any mixtures thereof, more preferably in the range of 1-100 µmol/ml and protamine or a protamine derivative, whereby the protamine derivative is preferably selected from protamine sulfate and protamine hydrochloride, or protamine-like peptides, or other cationic polymers, preferably hexadimethrine bromide (polybrene), that have the potential to neutralize the anti-coagulating effect(s) of heparine or heparine-like substances in a blood sample by charge interaction; but not comprising an activator of coagulation.

This kit may be used to perform an extrinsically activated test of a (potentially) heparin-inhibited citrated blood sample ('EX-test').

Preferably, in a kit according to the present invention, the kit comprises:
  a) a pipette tip containing constituent (A) comprising an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid; but not comprising a calcium salt; and
  b) a measurement cup containing constituent (B) comprising (1) a calcium salt, preferably $CaCl_2$, Calcium-Gluconate, or Calcium-Lactate or any mixtures thereof, more preferably in the range of 1-100 µmol/ml and (2) one or more platelet inhibitors, preferably selected from GPIIb/IIIa antagonists, preferably Abciximab, and/or cytoskeleton inhibitors, preferably Cytochalasin D and (3) protamine or a protamine derivative, whereby the protamine derivative is preferably selected from protamine sulfate and protamine hydrochloride, or protamine-like peptides, or other cationic polymers, preferably hexadimethrine bromide (polybrene), that have the potential to neutralize the anti-coagulating effect(s) of heparine or heparine-like substances in a blood sample by charge interaction; but not comprising an activator of coagulation.

This kit may be used to perform an extrinsically activated test with platelet inhibition of a heparin-inhibited citrated blood sample ('FIB-test').

Preferably, in a kit according to the present invention, the kit comprises:
  a) a pipette tip containing constituent (A) comprising an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid; but not comprising a calcium salt; and
b) a measurement cup containing constituent (B) comprising (1) a calcium salt, preferably $CaCl_2$, Calcium-Gluconate, or Calcium-Lactate or any mixtures thereof, more preferably in the range of 1-100 µmol/ml and (2) one or more lysis inhibitors, preferably aprotinine, tranexamic acid, or eaca and (3) protamine or a protamine derivative, whereby the protamine derivative is preferably selected from protamine sulfate and protamine hydrochloride, or protamine-like peptides, or other cationic polymers, preferably hexadimethrine bromide (polybrene), that have the potential to neutralize the anti-coagulating effect(s) of heparine or heparine-like substances in a blood sample by charge interaction; but not comprising an activator of coagulation.

This kit may be used to perform an extrinsically activated test with lysis inhibition of a citrated blood sample ('AP-test').

Preferably, in a kit according to the present invention, the kit comprises:
a) a pipette tip containing constituent (A) comprising an intrinsic activator of coagulation, which is preferably selected from celite, ellagic acid, sulfatit, kaolin, silica, RNA, or any mixtures thereof in dry, essentially dry, or liquid formulation, or in any other formulation that allows for dissolution of the activator within 30 s after aspiration of the sample liquid; but not comprising a calcium salt; and
b) a measurement cup containing constituent (B) comprising a calcium salt, preferably $CaCl_2$, Calcium-Gluconate, or Calcium-Lactate or any mixtures thereof, more preferably in the range of 1-100 µmol/ml; but not comprising an activator of coagulation.

This kit may be used to perform an intrinsically activated test of a citrated blood sample ('IN-test').

Preferably, in a kit according to the present invention, the kit comprises:
a) a pipette tip containing constituent (A) comprising an intrinsic activator of coagulation, which is preferably selected from celite, ellagic acid, sulfatit, kaolin, silica, RNA, or any mixtures thereof in dry, essentially dry, or liquid formulation, or in any other formulation that allows for dissolution of the activator within 30 s after aspiration of the sample liquid; but not comprising a calcium salt; and
b) a measurement cup containing constituent (B) comprising (1) a calcium salt, preferably $CaCl_2$, Calcium-Gluconate, or Calcium-Lactate or any mixtures thereof, more preferably in the range of 1-100 µmol/ml and (2) heparinase (heparin lyase) or other similar lyases that have the potential to neutralize the anti-coagulating effect(s) of heparine or heparine-like substances in a blood sample by direct chemical interaction; but not comprising an activator of coagulation.

This kit may be used to perform an intrinsically activated test of a heparin-inhibited citrated blood sample ('HEP-test').

Preferably, in a kit according to the present invention, the kit comprises:
a) a pipette tip containing constituent (A) comprising (1) an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid and (2) one or more heparin inhibitors, preferably protamine or protamine derivates, whereby preferred protamine derivatives include protamine sulfate and protamine hydrochloride, or other protamine-like peptides and their derivatives, or other cationic polymers, preferably hexadimethrine bromide (polybrene), that have the potential to neutralize the anti-coagulating effect(s) of heparine or heparine-like substances in a blood sample by charge interaction, preferably in a dry, essentially dry or a liquid formulation, or any other formulation that allows for dissolution of the reagent composition within 30 s after aspiration of the sample liquid; but not comprising a calcium salt; and
b) a measurement cup containing constituent (B) comprising a calcium salt, preferably $CaCl_2$, Calcium-Gluconate, or Calcium-Lactate or any mixtures thereof, more preferably in the range of 1-100 µmol/ml; but not comprising an activator of coagulation.

This kit may also be used to perform an extrinsically activated test of a (potentially) heparin-inhibited citrated blood sample ('EX-test').

Preferably, in a kit according to the present invention, the kit comprises:
a) a pipette tip containing constituent (A) comprising (1) an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid and (2) one or more heparin inhibitors, preferably protamine or protamine derivates, whereby preferred protamine derivatives include protamine sulfate and protamine hydrochloride, or other protamine-like peptides and their derivatives, or other cationic polymers, preferably hexadimethrine bromide (polybrene), that have the potential to neutralize the anti-coagulating effect(s) of heparine or heparine-like substances in a blood sample by charge interaction, preferably in a dry, essentially dry or a liquid formulation, or any other formulation that allows for dissolution of the reagent composition within 30 s after aspiration of the sample liquid and (3) one or more platelet inhibitors, preferably selected from GPIIb/IIIa antagonists, preferably Abciximab, and/or cytoskeleton inhibitors, preferably Cytochalasin D, in dry, essentially dry, or liquid formulation, or in any other formulation that allows for dissolution of the reagent composition within 30 s after aspiration of the sample liquid; but not comprising a calcium salt; and
b) a measurement cup containing constituent (B) comprising a calcium salt, preferably $CaCl_2$, Calcium-Gluconate, or Calcium-Lactate or any mixtures thereof, more preferably in the range of 1-100 µmol/ml; but not comprising an activator of coagulation.

This kit may also be used to perform an extrinsically activated test with platelet inhibition of a heparin-inhibited citrated blood sample ('FIB-test').

Preferably, in a kit according to the present invention, the kit comprises:
a) a pipette tip containing constituent (A) comprising (1) an extrinsic activator of coagulation, which is preferably selected from TissueFactor (TF), lipidated TF or recombinant TF or any mixtures thereof in dry, essentially dry, or liquid formulation or in any other formulation that allows for dissolution of the TF within 30 s after aspiration of the sample liquid and (2) one or more heparin inhibitors, preferably protamine or protamine derivates, whereby preferred protamine derivatives include protamine sulfate and protamine hydrochloride, or other protamine-like peptides and their derivatives, or other cationic polymers, preferably hexadimethrine bromide (polybrene), that have the potential to neutralize the anti-coagulating effect(s) of heparine or heparine-like substances in a blood sample by charge interaction, preferably in a dry, essentially dry or a liquid formulation, or any other formulation that allows for dissolution of the reagent composition within 30 s after aspiration of the sample liquid and (3) one or more lysis inhibitors, preferably aprotinine, tranexamic acid or eaca, in dry, essentially dry, or liquid formulation, or in any other formulation that allows for dissolution of the reagent composition within 30 s after aspiration of the sample liquid; but not comprising a calcium salt; and b) a measurement cup containing constituent (B) comprising a calcium salt, preferably $CaCl_2$, Calcium-Gluconate, or Calcium-Lactate or any mixtures thereof, more preferably in the range of 1-100 μmol/ml; but not comprising an activator of coagulation.

This kit may also be used to perform an extrinsically activated test with lysis inhibition of a citrated blood sample ('AP-test').

Also preferably, in a kit according to the present invention, the kit comprises the same constituents as described above, but with constituent A being constituent B and constituent B being constituent A. In other words, it is also preferred that the kit according to the present invention comprises the same combinations of components as described above, but with the components, which are according to the above description comprised by the tip, are in this embodiment comprised by the cup and the components, which are according to the above description comprised by the cup, are in this embodiment comprised by the tip.

This means, for example, for the above firstly described 'EX-test', that the kit may also comprise an extrinsic activator stored in the cup and the Calcium salt and the heparin inhibitor stored in the tip; for the secondly described 'EX-test', the kit may also comprise of an extrinsic activator and a heparin inhibitor stored in the cup and the Calcium salt stored in the tip. The kit to perform an 'FIB-test' may also comprise an extrinsic activator stored in the cup and the Calcium salt, the heparin inhibitor and the platelet inhibitor(s) stored in the tip; or, it may also comprise an extrinsic activator, the platelet inhibitor(s) and the heparin inhibitor stored in the cup and the. Calcium salt stored in the tip. The kit to perform an 'AP-test' may also comprise an extrinsic activator stored in the cup and the Calcium salt, the lysis inhibitor(s) and the heparin inhibitor stored in the tip; or, it may also comprise an extrinsic activator, the lysis inhibitor(s) and the heparin inhibitor stored in the cup and the Calcium salt stored in the tip. The kit to perform an 'IN-test' may also comprise an intrinsic activator stored in the cup and the Calcium salt stored in the tip. The kit to perform an 'HEP-test' may also comprise an intrinsic activator stored in the cup and the Calcium salt and the heparin inhibitor stored in the tip; or, it may also comprise an intrinsic activator and the heparin inhibitor stored in the cup and the Calcium salt stored in the tip.

Finally, also combinations of the above described embodiments are preferred to perform certain viscoelastic tests. For example, the cup or tip may contain both, extrinsic and intrinsic, coagulation activator.

Taken together, one of the several advantages of the kit according to the present invention is that the constituent (A) contained in the pipette tip and the constituent (B) contained in the measurement cup can be optimized with regard to the long-term stability of the kit. For example, if the TF has less stability when mixed with hexadimethrine bromide (polybrene) in liquid phase, the TF can be placed in the tip and the hexadimethrine bromide (polybrene) can be placed together with the calcium salt in the cup or vice versa. For example, if the TF has also less stability when mixed with Cytochalasin D in the liquid phase, Cytochalasin D can also be placed in the cup. For example, if Cytochalasin D has less stability when mixed with hexadimethrine bromide (polybrene) in liquid phase, it can be dried together with the calcium salt and hexadimethrine bromide (polybrene). Or, it can be dried together with the TF in the tip.

Thus, the kit according to the present invention provides a considerable variety of options to increase reagent stability to the required level. This is achieved without the need for new automation technology for reagent filling or reagent handling and without adding new substances to the reagent composition.

Moreover, the separation into two constituents (A) and (B) allows for a longer incubation time of those ingredients that are placed in the tip (dependent on the time lag between aspiration of sample liquid into the tip and release of sample liquid into the cup). For example, the more complex biological activator molecules like TF or ellagic acid could have more time for proper reconstitution if they are stored in the tip (e.g., to restore their equilibrium quaternary protein structure or to form uniformly sized micelles within the lipid-containing sample). Accordingly, their activity will be more consistent from test to test when compared to other reagent compositions where activator and mediating $Ca^{2+}$ are mixed, preferably dissolved, simultaneously.

Furthermore, it is preferable that the constituent (A) and/or the constituent (B) described herein additionally comprise a coagulation factor, preferably selected from FI, FII, FV, FVII, FVIII, FIX, FX, FXI, and FXIII or a coagulation inhibitor, preferably selected from TFPI, ATIII and APC. If the factors or inhibitors are comprised by constituent (A), i.e. placed into the tip, they will also benefit from the increased incubation time as described above and yield more consistent results from test to test.

Method

In a second aspect the present invention provides a method of performing a viscoelastic analysis on a sample, comprising the following steps:

(1) providing a diagnostic kit according to the present invention as described above;

(2) aspirating a sample into the pipette tip of the diagnostic kit as described above, thereby mixing, preferably dissolving, the constituent (A) contained in said pipette tip in the sample and obtaining a mixture, preferably a solution, of sample and constituent (A);

(3) transferring the mixture of said sample and said constituent (A) into the measurement cup containing constituent (B), and obtaining a mixture, preferably a solution, of said sample, said constituent (A) and said constituent (B), wherein in said mixture constituent (A) and constituent (B) form a diagnostic composition comprising as a component (i) an activator of coagulation and as a component (ii) a calcium salt;

(4) optionally, putting the measurement cup into an apparatus suitable for performing a viscoelastic analysis; and (5) performing the viscoelastic analysis of said mixture in the measurement cup.

The sample is preferably a blood sample, more preferably mammalian, more preferably a sample of human blood or blood components, for example whole blood or blood plasma.

The apparatus suitable for performing a viscoelastic analysis is preferably a device as described in U.S. Pat. No. 5,777,215 A or in 6,537,819 B2. Another preferred example of an apparatus suitable for performing a viscoelastic analysis is schematically shown in FIG. 2.

In more general, as used herein a viscoelastic analysis (also referred to as viscoelastic measurement) refers to a (viscoelastic) analysis of a sample, in particular a blood sample or a sample of blood elements, e.g. plasma or cells, in order to determine its coagulation characteristics, wherein such a viscoelastic analysis in the broadest sense is the measurement of a relative movement of a cuvette containing a blood sample relative to a pin. In particular, in a typical viscoelastic analysis a dot is formed between measurement cup and pin and thereafter the clot itself is stretched by the movement of the pin relative to the cup. The detection of the characteristic parameters of the clot is based on the mechanical coupling of cup and pin by the clot. In particular, a viscoelastic measurement provides information about several distinct parameters, for example the time between coagulation activation and clot initiation (clotting time CT), the dynamics of clot formation (clot formation time CFT), the firmness of the clot (amplitudes A5-A30 and maximum clot firmness MCF), and/or the extent of fibrinolysis (maximum lysis ML). Thus, the viscoelastic analysis preferably comprises the determination of the clotting time, the clot formation time, and/or the firmness of the clot over time including fibrinolytic effects. An exemplary diagram showing a typical viscoelastic analysis (also referred to as viscoelastic measurement) and the meaning of the parameters mentioned above is shown in FIG. 1. The clotting time CT is the initial lag time until the firmness starts to build up. The amplitude values A5-A30 are the firmness values 5-30 minutes after CT. The maximum lysis is the percentage decrease of firmness after the maximum value (MCF) was reached.

The positioning of the measurement cup into an apparatus suitable for performing a viscolelastic analysis (step (4)) is optional, since it may also occur at any time before. For example, all pipetting can also be performed while the cup is in the apparatus, if the apparatus provides enough access to the upper open end of the cup while placed in measurement position.

Preferably, the method of performing a viscoelastic analysis on a sample according to the present invention further comprises a step (2-a) that follows step (2) and precedes step (3), wherein the tip is kept on the pipette for 1-30 s, preferably from 1-5 s. Thereby, a better or even complete reagent dissolution is allowed. Accordingly, in step (2-a) a short time delay of e.g. 1-30 s allows for complete dissolution of constituent (A) of the diagnostic composition within the sample.

Preferably, each of steps (2) and (3) of the method of the present invention takes less than 30 sec, more preferably each of steps (2) and (3) takes from 2 to 10 s. Thereafter, the mixture of the sample and the diagnostic composition in the cup is preferably quickly transferred to the measuring apparatus, more preferably in less than 30 s.

It is also preferred in the method according to the present invention that the method further comprises a step (3-a) following step (3) and preceding step (4), wherein in step (3-a) the mixture is at least partially re-aspirated into the pipette tip and subsequently released again into the measurement cup. This step may be repeated one or more, e.g. 2, 3, 4, 5, 6, 7, 8, 9, or 10 times. Thereby a better mixing of the sample is achieved and a better dissolution of constituent (B) is allowed.

Preferably, the analysis in step (5) comprises the determination of the clotting time, the clot formation time, the firmness of the clot overtime, fibrinolysis activity (obtained as percentage of firmness reduction in relation to the maximum clot firmness), and/or any combination thereof.

If dissolution of the reagent in the cup is faster than 20 seconds, a mixing step (re-aspirating step (3-a)) is not necessarily required and the user has only to perform two pipetting steps in total for each test (compared to up to eight steps required for a liquid reagent system). Furthermore, no change of pipette tip is necessary when preparing one test. This shows the direct benefit of the present invention for the person who is performing such tests regarding the ease of use.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Effect of TF/Phospholipids Deposited in the Measurement Cup Alone or in Combination with $CaCl_2$ on Clotting Time To investigate the effect of the extrinsic activator of coagulation TF and phospholipids deposited in dry form in the measurement cup either alone or in combination with $CaCl_2$ on the clotting time, viscoelastic measurements of human plasma samples (10 donors mixed) were performed with a ROTEG® 05 device (Pentapharm GmbH, Munich, Germany). Frozen plasma samples where freshly thawed and heated to 37° C. just before measurement. The source of TF was Innovin® (Siemens AG, Germany) and the source of CaCl2 was Calcium Chloride Dihydrate (Sigma-Aldrich Chemie GmbH, Germany). Pipetting was performed with Top-Line® 1 ml tips (AHN Biotechnologie GmbH, Germany) on an electronic E-Line® pipettor (Biohit Oyj, Finland). For the control experiment, the same sample was measured by using the standard liquid reagent provided for the ROTEG® 05 system (TEM Innovations GmbH, Germany).

Results are shown in Table 1 below.

TABLE 1

Clotting times obtained after drying similar amounts of TF solution in the measurement cup and storing for one week at room temperature. For the pure TF sample, the same amount of $CaCl_2$ as in the mixed sample was added just before the measurement (each value was calculated as average of 4 measurements with human plasma). Mixed storage of TF and $CaCl_2$ impairs the clotting time CT severely (correction impossible), while increasing the amount of TF by a factor of 4 and adding 2% sucrose can compensate for degradation of the pure TF sample during storage.

| Activator | CT control | CT of TF/CaCl$_2$ mixture | CT of pure TF | CT of pure TF (4x concentr.) |
|---|---|---|---|---|
| Tissue factor/ phospholipids | 56 sec | >800 sec | 126 sec | 58 sec |

Example 2: Effect of Ellagic Acid/Phospholipids Deposited in the Pipette Tip in Either Wet or Dry Form on Clotting Time To investigate the effect of the intrinsic activator of coagulation ellagic acid and phospholipids deposited either in dry or in wet form in the pipette tip on the clotting time, viscoelastic measurement were performed by using the equipment and procedures described above.

Results are shown in Table 2 below.

TABLE 2

Clotting times (CT) obtained by similar activator solutions without additives after storage as liquid or dried tip for 7 days at room temperature (tip insert made from polyether, each value was calculated as average of 4 measurements with human plasma). The wet storage of ellagic acid results in comparable CT values as the control, but the degradation during dry storage can be compensated for by 35% more activator content and adding 2% sucrose.

| Activator | CT control | CT of dry tip | CT of wet tip | CT of dry tip (1.3x concentr.) |
|---|---|---|---|---|
| Ellagic acid/ phospholipids | 164 sec | 258 sec | 162 sec | 161 sec |

Example 3: Effect of CaCl$_2$ Deposited in the Pipette Tip in Either Wet or Dry Form or in the Measurement Cup in Dry Form on Clotting Time To investigate the effect of the intrinsic activator of coagulation ellagic acid and phospholipids deposited either in dry or in wet form in the pipette tip or in dry form in the measurement cup on the clotting time, viscoelastic measurement were performed by using the procedures and equipment as described above.

Results are shown in Table 3 below.

TABLE 3

Clotting times (CT) obtained after storing CaCl2 in the tip and the cup after drying for one week at room temperature or storing as liquid in the tip (tip insert made from polyether; each value was calculated as average of 4 measurements with human plasma). No significant differences to the control CT are observed for all three approaches.

| Activator | CT control | CaCl$_2$ dried in tip | CaCl$_2$ wet in tip | CaCl$_2$ dried in cup |
|---|---|---|---|---|
| Ellagic acid | 198 sec | 193 sec | 202 sec | 204 sec |

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 3a,b,c shows schematic cross-sectional views of three preferred embodiments of a pipetting tip (11a, 11b, 11c) containing constituent (A), wherein the constituent (A) is kept in a porous insert:

Figure 1:
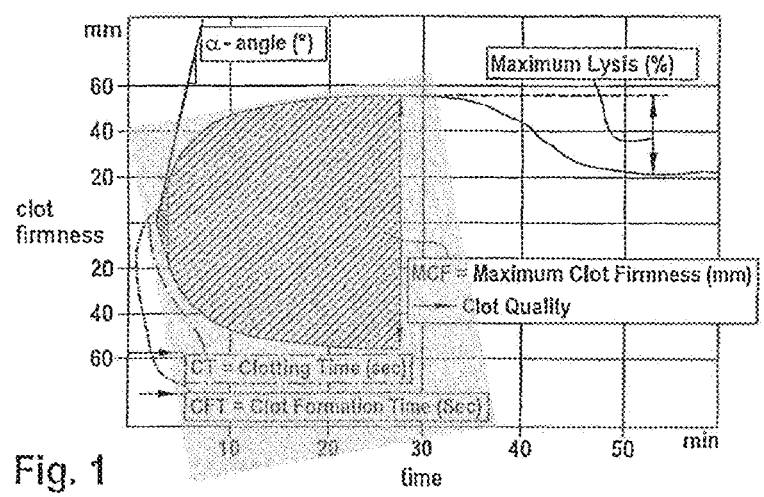
FIG. 1 is an exemplary diagram showing a typical viscoelastic measurement and corresponding curve parameters: clotting time CT is the lag time between activation of the sample and the time when a firmness value of 2 mm is reached; clot formation time CFT is the time that passes between the firmness values of 2 mm and 20 mm; alpha is the angle that is formed between the tangential of the firmness curve and the x-axis; maximum clot firmness MCF is the maximum firmness value of the curve; maximum lysis is the percentage decrease of firmness after MCF has been reached.
Figure 2:
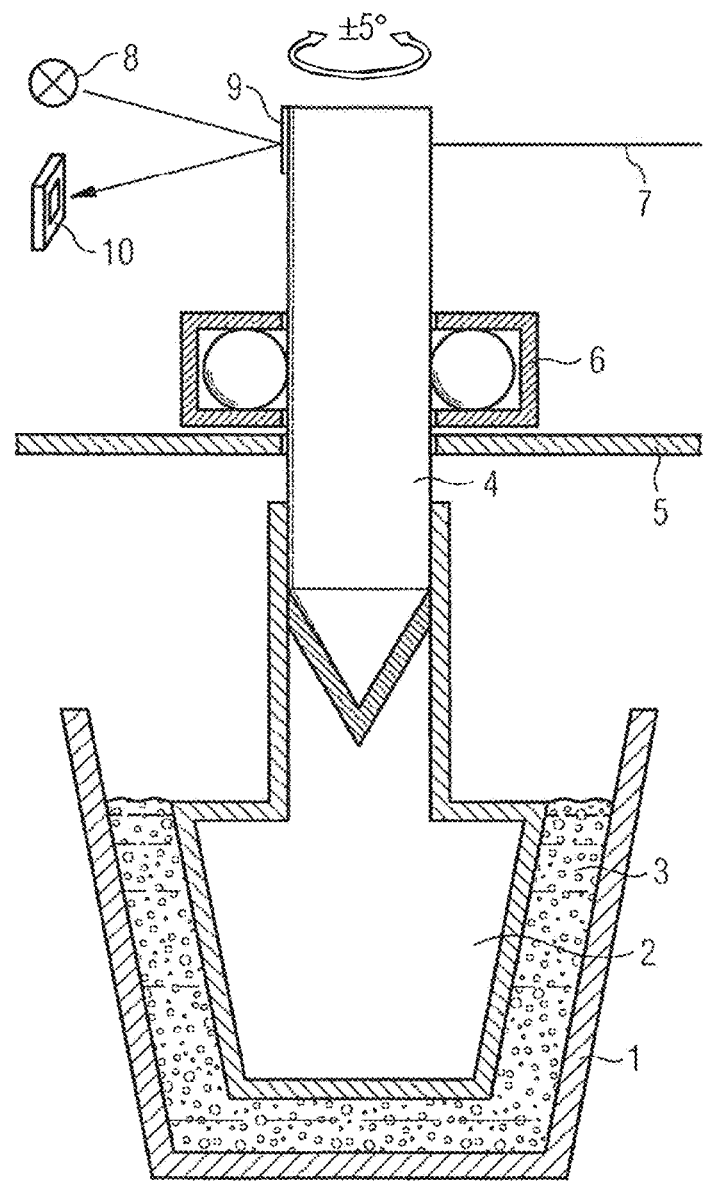
FIG. 2 shows an illustration of an apparatus for viscoelastic testing: After the formation of the clot between cup 1 (cuvette) and pin 2, the clot itself is stretched by the movement of the pin 2 relative to the cup 1. The detection of the characteristic parameters of the clot is based on the mechanical coupling of cup 1 and pin 2 by the clot. This is only possible if the clot adheres on the surfaces of both cup 1 and pin 2. Thus, a firm adhesion to the surfaces of both cup 1 and pin 2 is typically required for the viscoelastic analysis. During a viscoelastic measurement, the pin is fixed to the axis 4 and gently and slowly rotated in the cup via the spring 7. The axis 4 itself is fixed to the base plate 5 with the ball bearing 6. The movement of the pin is measured optically by illuminating the mirror 9 (fixed to the axis 4) with the light source 8 and detecting the reflected signal at the spatially resolving photo detector 10.

a) regular tip shape with open lower end (12a), open upper end (13a) fitting to the pipette dimensions, and porous insert (14a) with a conical shape as required by the regular tip shape;
b) adapted tip shape with open lower end (12b), open upper end (13b) fitting to the pipette dimensions, and porous insert (14b) with cylindrical shape as required by the adapted tip shape;
c) adapted tip shape with open lower end (12c), open upper end (13c) fitting to the pipette dimensions, and layer of at least two porous inserts (14c) with cylindrical shapes as required by the adapted tip shape.

FIG. 4a,b,c shows schematic cross-sectional views of three preferred embodiments of a measurement cup (1a, 1b, 1c) containing constituent (B):
  a) Normal cup (1a) with dry constituent (B) (15a) unevenly distributed on the bottom (thicker range along the edge due to capillary forces during the drying). The dotted line (16a) indicates the filling level of the sample.
  b) Normal cup (1b) with dry constituent (B) (15b) evenly distributed on the bottom and sidewalls after being sprayed in micro-drops onto the surface. The dotted line (16b) indicates the filling level of the sample.
  c) Adapted cup (1c) with dry constituent (B) (15c) evenly distributed on the bottom because rounded edges reduce capillary forces during drying. The dotted line (16c) indicates the filling level of the sample.

LIST OF REFERENCE SIGNS 1, 1a, 1b, 1c measurement cup
2, 2a, 2b, 2c pin
3 sample
4 axis
5 base plate
6 ball bearing
7 spring
8 light source
9 mirror
10 detector
11, 11a, 11b, 11c pipette tip
12a, 12b, 12c open lower end of the pipette tip
13a, 13b, 13c open upper end of the pipette tip
14a, 14b, 14c porous insert(s)
15a, 15b, 15c constituent (B) in (essentially) dry form deposited on the inner wall of the measurement cup 1a, 1b, 1c
16a, 16b, 16c dotted line indicating the filling level of the sample

What is claimed is:

1. A diagnostic kit for viscoelastic analysis of a sample comprising:
  a) a pipette tip having an interior surface adapted to come into contact with the sample and containing constituent (A); and
  b) a measurement cup having an interior surface adapted to come into contact with the sample and containing constituent (B),
    wherein the constituent (A) is different from the constituent (B),
    wherein the constituents (A) and (B) are adapted to form a diagnostic composition upon combination, and
    wherein the diagnostic composition comprises at least the following components (i) and (ii):
      i) An activator of coagulation; and
      ii) A calcium salt
    wherein the pipette tip containing the constituent (A) does not contain the constituent (B);
    and wherein the measurement cup containing the constituent (B) does not contain the constituent (A), wherein
      1) Constituent (A) comprises component (i) but not component (ii) and constituent (B) comprises component (ii) but not component (i); or
      2) Constituent (A) comprises component (ii) but not component (i) and constituent (B) comprises component (i) but not component (ii)
    wherein each of the constituent (A) and (B) is independently from each other an essentially dry formulation or a dry formulation, and
    wherein constituent (B) is disposed on the interior surface of the measurement cup, and constituent (A) is disposed in fixed relation to the interior surface of the pipette tip.

2. The diagnostic kit according to claim 1, wherein the kit does not comprise a further reagent container in addition to the pipette tip containing a constituent (A) and the measurement cup containing a constituent (B).

3. The diagnostic kit according to claim 1, wherein the activator of coagulation is an extrinsic activator and/or an intrinsic activator.

4. The diagnostic kit according to claim 3, wherein the extrinsic activator is a Tissue Factor (TF).

5. The diagnostic kit according to claim 3, wherein the intrinsic activator of coagulation is selected from the group consisting of celite, ellagic acid, sulfatit, kaolin, silica, RNA, and mixtures thereof.

6. The diagnostic kit according to claim 3, wherein the extrinsic activator is selected from the group consisting of lipidated TF, rTF, and combinations thereof.

7. The diagnostic kit according to claim 1, wherein the calcium salt is calcium chloride and/or calcium lactate and/or calcium gluconate.

8. The diagnostic kit according to claim 1, wherein the diagnostic composition comprises one or more components selected from the group consisting of a coagulating activating factor, a coagulation inhibitor, and an active-component inhibitor.

9. The diagnostic kit according to claim 1, wherein the diagnostic composition comprises one or more components selected from the group consisting of one or more platelet inhibitors, fibrinolysis inhibitors, and heparin inhibitors.

10. The diagnostic kit according to claim 1, wherein the diagnostic composition comprises one or more components selected from the group consisting of a cytoskeleton inhibitor and a GPIIb/IIIa antagonist.

11. The diagnostic kit according to claim 1, wherein the diagnostic composition comprises one or more components selected from the group consisting of aprotinin, tranexamic acid, eaca, thrombin-activated fibrinolysis inhibitor, plasminogen activation inhibitor 1/2, α2-antiplasmin, and α2-macroglobulin.

12. The diagnostic kit according to claim 1, wherein the diagnostic composition comprises one or more components selected from the group consisting of heparinase, protamine or protamine-related peptides and their derivatives, hexadimethrine bromide (polybrene), and other cationic polymers.

13. The diagnostic kit according to claim 1, wherein the diagnostic composition comprises one or more components selected from the group consisting of FI, FII, FV, FVII, FVIII, FIX, FX, FXI, FXIII, and TF.

14. The diagnostic kit according to claim 1, wherein the diagnostic composition comprises one or more components selected from the group consisting of a tissue factor pathway inhibitor, antithrombin I-IV, and activated protein C.

15. The diagnostic kit according to claim 1, wherein the diagnostic composition comprises one or more components selected from the group consisting of a phospholipid, a heparin inhibitor, heparinase, hexadimethrine bromide (polybrene), wherein the one or more components are comprised by constituent (A) and placed in the reagent-containing tip.

16. The diagnostic kit according to claim 1, wherein a protein stabilizer is comprised by constituent (A) but is not comprised by constituent (B); or wherein a protein stabilizer is comprised by constituent (B) but is not comprised by constituent (A).

17. The diagnostic kit according to claim 1, wherein the pipette tip containing the constituent (A) comprises at least one porous insert with pore sizes from 3 to 500 micrometers, wherein the insert holds constituent (A) in fixed relation to the interior surface of the pipette.

18. The diagnostic kit according to claim 17, wherein the shape of the pipette tip containing the constituent (A) is adapted to receive a porous insert in its lower part, such that the porous insert abuts the interior surface of the pipette tip.

19. The diagnostic kit according to claim 17, wherein the shape of the pipette tip containing the constituent (A) is adapted to receive a porous insert in its lower part, wherein the porous insert has a cylindrical shape.

20. The diagnostic kit according to claim 1, wherein the measurement cup containing a constituent (B) comprises a reagent layer having an even thickness on a bottom and, at least partially, a minimum height of 2 mm at a sidewall.

21. The diagnostic kit according to claim 1, wherein the measurement cup containing a constituent (B) has rounded edges along a contact line between a bottom and a sidewall.

22. A method of performing a viscoelastic analysis on a sample, comprising the following steps:
   1) providing a diagnostic kit according to claim 1;
   2) aspirating a sample into the pipette tip of the diagnostic kit, thereby mixing the constituent (A) contained in said pipette tip in the sample and obtaining a mixture of the sample and constituent (A);
   3) transferring the mixture of said sample and said constituent (A) into the measurement cup containing constituent (B), and obtaining a mixture of said sample, said constituent (A) and said constituent (B), wherein in said mixture constituent (A) and constituent (B) form a diagnostic composition comprising as a component (i) an activator of coagulation and as a component (ii) a calcium salt;
   4) putting the measurement cup into an apparatus suitable for performing a viscoelastic analysis; and
   5) performing the viscoelastic analysis of said mixture in the measurement cup.

23. The method according to claim 22, wherein the sample is a human blood sample and comprises whole blood and/or blood plasma.

24. The method according to claim 22, wherein the analysis in step (5) comprises the determination of the clotting time, the clot formation time, the firmness of the clot over time or the fibrinolysis activity as firmness reduction in relation to the maximum clot firmness, or any combination thereof.

25. The diagnostic kit according to claim 1, wherein the measurement cup is adapted to placed into an apparatus suitable for performing a viscoelastic analysis, wherein a viscoelastic analysis of the sample is performed in the measurement cup.

* * * * *